United States Patent
Koshti et al.

(10) Patent No.: US 10,015,963 B2
(45) Date of Patent: *Jul. 10, 2018

(54) MICROEMULSIONS OF LIPIDATED GLYCINES AND PHENOXY ETHANOL FOR PRESERVATION OF PERSONAL CARE PRODUCTS

(71) Applicant: GALAXY SURFACTANTS LTD., Navi Mumbai (IN)

(72) Inventors: Nirmal Koshti, Piscataway, NJ (US); Bhagyesh Jagannath Sawant, Kalyan (IN); Santosh Vishnu Kadam, Navi Mumbai (IN); Srinivas Uppalaswamy Pilli, Kamothe (IN); Devyani Ashok Mali, Ambernath (IN); Shraddha Kiran Ratnaparkhe, Thane (IN); Pooja Vaidya Kshirsagar, Nagpur (IN)

(73) Assignee: GNA Surfactants Ltd., New Mumbai, Maharashtra (IN)

(*) Notice: Subject to any disclaimer, the term of this patent is extended or adjusted under 35 U.S.C. 154(b) by 0 days.

This patent is subject to a terminal disclaimer.

(21) Appl. No.: 15/125,064

(22) PCT Filed: Jun. 12, 2014

(86) PCT No.: PCT/IN2014/000394
§ 371 (c)(1),
(2) Date: Sep. 9, 2016

(87) PCT Pub. No.: WO2015/136546
PCT Pub. Date: Sep. 17, 2015

(65) Prior Publication Data
US 2017/0020131 A1    Jan. 26, 2017

(30) Foreign Application Priority Data
Mar. 10, 2014 (IN) .......................... 800/MUM/2014

(51) Int. Cl.
*A01N 37/46* (2006.01)
*A61Q 19/00* (2006.01)
(Continued)

(52) U.S. Cl.
CPC ............. *A01N 37/46* (2013.01); *A01N 25/04* (2013.01); *A01N 31/14* (2013.01); *A61K 8/062* (2013.01);
(Continued)

(58) Field of Classification Search
None
See application file for complete search history.

(56) References Cited

U.S. PATENT DOCUMENTS 5,736,574 A    4/1998 Burnier
6,296,858 B1   10/2001 Agostini et al.
(Continued)

FOREIGN PATENT DOCUMENTS

JP    49093521 A    9/1974
WO    1999027902    6/1999
(Continued)

OTHER PUBLICATIONS

Azeem et al. (Emerging Role of Microemulsions in Cosmetics, Bentham Science, vol. 2, Issue 3, 2008, pp. 275-289).*
(Continued)

*Primary Examiner* — Robert A Wax
*Assistant Examiner* — Melissa S Mercier
(74) *Attorney, Agent, or Firm* — Kramer Amado, P.C.

(57) ABSTRACT

Optically isotropic, thermodynamically and chemically stable microemulsions of antimicrobials comprising of mixtures of N-undecylenoyl glycine, N-caryloyl glycine and 2-phenoxy ethanol for preservation of personal care products are described herein. They offer a broad spectrum of antimicrobial activity by inhibiting the growth of bacteria as
(Continued)

well as fungi that can otherwise flourish in personal care products rendering them unsuitable for the use. The personal care products that can be preserved by these microemulsions of antimicrobials are, gels, serums, solutions, lotions, creams, emulsions, wet wipes and the like, containing water in varying amount.

8 Claims, 2 Drawing Sheets

(51) Int. Cl.
| | |
|---|---|
| *A01N 25/04* | (2006.01) |
| *A01N 31/14* | (2006.01) |
| *A61K 8/34* | (2006.01) |
| *A61K 8/44* | (2006.01) |
| *A61Q 5/02* | (2006.01) |
| *A61K 8/06* | (2006.01) |
| *A61K 8/362* | (2006.01) |
| *A61K 8/37* | (2006.01) |
| *A61K 8/42* | (2006.01) |
| *A61K 8/46* | (2006.01) |

(52) U.S. Cl.
CPC ............... *A61K 8/068* (2013.01); *A61K 8/34* (2013.01); *A61K 8/362* (2013.01); *A61K 8/375* (2013.01); *A61K 8/42* (2013.01); *A61K 8/44* (2013.01); *A61K 8/463* (2013.01); *A61Q 5/02* (2013.01); *A61Q 19/00* (2013.01); *A61K 2800/262* (2013.01)

(56) References Cited

U.S. PATENT DOCUMENTS

| | | | |
|---|---|---|---|
| 7,214,391 B2 | 5/2007 | McDonald | |
| 2002/0058010 A1* | 5/2002 | Picard-Lesboueyries | A61K 8/0295 424/43 |
| 2004/0096528 A1 | 5/2004 | Miser et al. | |
| 2013/0101530 A1* | 4/2013 | Koshti | A61K 8/33 424/59 |

FOREIGN PATENT DOCUMENTS

| | | |
|---|---|---|
| WO | 2007104879 | 9/2007 |
| WO | 2013/076697 A2 | 5/2013 |

OTHER PUBLICATIONS

Sentry, What does pH-balanced mean?; accessed Oct. 29, 2017).*
International Search Report dated Feb. 23, 2015 for PCT/IN2014/000394.
Anonymous, "New cosmetic formulations", Research Disclosure Database No. 443043, published in the Mar. 2001 paper journal (disclosed anonymously).
Badreshia, et al., "Iodopropynyl Butylcarbamate", Am. J. of Contact Dermatitis, vol. 13, No. 2 (Jun. 2002); pp. 77-79.
Degroot, "Isothiazolinone Preservative Cause of a Continuing Epidemic of Cosmetic Dermatitis", The Lancet, Feb. 11, 1989, pp. 314-316.
Du, et al., "In Vitro Neurotoxicity of Methylisothiazolinone, a Commonly Used Industrial and Household Biocide, Proceeds via a Zinc and Extracellular Signal-Regulated Kinase Mitogen-Activated Protein Kincase0Dependent Pathway", The Journal of Neuroscience, Sep. 1, 2002 (22(17): 7408-7416.
Harvey, "Endocrine Disrupters and Human Health: Could Oesetrogenic Chemicals in Body Care Cosmetics Adversely Affect Breast Cancer Incidence in Women?", Journal of Applied Toxicology 24 (2004) 167-176.
Kang, et al., "Decreased Sperm Number and Motile Activity on the F1 Offspring Maternally Exposed to Butyl p-Hydroxybenzoic Acid (Butyl Paraben)", J. Vet. Med. Sci., vol. 64(3); Toxicology Full Paper (Aug. 8, 2001); pp. 227-235.
Kumar, et al., "Alteration of testicular steroidogenesis and histopathology of reproductive syste in male rates treated with triclosan", Reproductive Toxicology 27 (2009) 177-185.
Pedersen, "The Preservatives Ethyl-, Propyl-, and Butylparaben are Oestrogenic in an in vivo Fish Assay", Pharmacology & Toxicology 2000, 86, 110-113.
Proserpio, et al., "Nonpreservative substances able to inhibit microbial growth in cosmetics", Cosmetics & Toiletries, Edizione Italiana (1996) 17(3); 11-13, 16-19.
Routledge, "Some Alkyl Hydroxy Benzoate Preservatives (Parabens) are Estrogenic", Toxicology and Applied Pharmacology 23 (1998) 12-19.
Zorilla, "The Effects of Triclosan on Puberty and Thuroid Hormones in Male Wistar Rats", Toxicological Sciences 107(1), 56-64 (2009).

* cited by examiner

MICROEMULSIONS OF LIPIDATED GLYCINES AND PHENOXY ETHANOL FOR PRESERVATION OF PERSONAL CARE PRODUCTS

FIELD OF INVENTION

The present invention relates to chemically and thermodynamically stable microemulsions, also sometimes described as micellar solutions, for preservation of personal care formulations. These compositions offer a broad spectrum of activity against the microbes and are based on well-known, universally accepted anti-microbial and personal care ingredients. The highly effective microemulsions of the instant invention do not employ any controversial antimicrobials such as parabens, halogenated antimicrobials, isothiazolinones, phenolic compounds and formaldehyde releasing substances.

BACKGROUND OF INVENTION

Preserving personal care products from microbial degradation is quite challenging. Most topical cosmetics and dermatological products in the form of creams, lotions, gels, shampoos, body-washes and face-washes contain significant amount of water in them that provides a very hospitable environment for the microbial growth. In addition to water, the other cosmetic ingredients can also be a good source of nutrients to microbes. Another pertinent point to be reckoned here is that the shelf-life of the personal care products and the period after opening the container by the consumer is quite long compared to pharmaceutical products or food products. Unlike pharmaceuticals, cosmetic products are neither sterilized and nor packed in hermetic conditions. Thus, the requirement for the preservation of the personal care products is indeed quite challenging. This is further compounded by the limited choice of antimicrobials since the available approved antimicrobials are very few and those which have good antimicrobial activity are quite toxic. Consumers want products meant for topical applications to be free from toxic antimicrobials that are used as preservatives. All the current very effective antimicrobials are involved in serious controversies. For example, parabens are implicated in disrupting endocrine system, ultimately linked to breast cancer [(*Pharmacology & Toxicology* (Vol. 86(3), pp 110-13, March 2000, *Toxicology and Applied Pharmacology* (Vol. 153(1), pp. 12-19 (November 1998), *Journal of Veterinary Medical Science* (Vol. 64(3), pp. 227-35 (March 2002, *Journal of Applied Toxicology*, 24 (3): 167-176, (2004)]. Formaldehyde is classified as Category 3 CMR (carcinogenic, mutagenic and reproductive toxicity) and hence all formaldehyde releasers are under the cloud. This class includes the work-horse preservatives like DMDM hydantoin, diazolidinyl urea, imidazolidinyl urea and Quaternary 15.

Another class of very effective antimicrobials is 'isothiazolinones'. Methyl and Chloromethyl isothiazolinones have been used in personal care but they have been reported to be neurotoxic and skin sensitizers (*Journal of Neuroscience* 22 (17): 7408-7416. *The Lancet*, Volume 333, Issue 8633, Pages 314-316 (1989).

Halogenated molecules have their own share of controversies. For example, there is a big movement against triclosan. It is a phenolic and halogenated molecule and has been implicated in ecotoxicity (algae, dolphins). It is reported to be an endocrine disrupter (thyroid function) and is reported to impair cardiac and skeletal muscles. There seems to a special concern for children who are at higher risk of allergies and the immune systems (Toxicological Sciences, 2009, 107 (1): 56-64, Reproductive Toxicology, April 2009, 27(2):177-185). Company like Johnson and Johnson has removed it from its products and P & G will be doing the same by the end of 2014. Reckitt Benckiser is phasing it out from its products too. Iodopropynyl butyl carbamate, another halogenated antimicrobial, is a contact allergen (*American Journal of contact dermatitis* 13(2), 77-79 (2002). Presence of iodine in the molecular structure gets it implicated in Goiter and malfunctioning thyroid gland. It has not been allowed in Japan and in European Union (EU) it is allowed only up to 0.02% in leave-on products. Similarly, EU permits usage of methyl dibromo glutaronitrile only up to 0.1% and that too in only rinse-off products. Halogenated molecule like Bronopol, very widely used once upon a time, however, is banned today in countries like Canada for its usage in cosmetics. It is involved in allergic reactions as well as generation of N-nitroso amine that are known to be carcinogenic. The quaternary ammonium compounds (examples are cetyl pyridinium chloride, benzethonium chloride, benzalkonium chloride) exhibit good antimicrobial activity but their utility in personal care industry is limited due to specific incompatibilities with other cosmetic ingredients, particularly with the ingredients of strong anionic nature.

In summary, the major work-horse preservatives of personal care industry are being phased out and industry is looking for a solution, a preservation system that is efficacious, safe and globally accepted. The antimicrobials available to personal care industry other than these five major classes of work-horses (parabens, isothiazolinones, formaldehyde releasers, halogenated molecules and quaternary ammonium compounds) are too weak and have a number of limitations. Hence it is important to find a good antimicrobial synergy between non-controversial antimicrobials and other accepted personal care ingredients to offer a broad spectrum of activity against bacteria and fungi meeting the purpose of preservation of finished personal care formulations.

Both, personal care industry and the manufacturers of preservatives are looking for better and safer alternatives for preservation of personal care products. Though discovering a new powerful and toxicologically safe broad spectrum antimicrobial is theoretically possible, it is a long and expensive process to discover a new material and have it approved by the Cosmetics Directives and accepted by the global markets. According to the industry experts, finding an 'ideal preservative' is like looking for the biblical "Holy Grail" and the industry has stopped looking for the 'ideal' preservative (Donald Orth in 'Insights into cosmetic microbiology', Allured Publications, 2010).

Thus, faced with a consumer rebellion against certain categories of preservatives, much of the current effort by the industry has been directed in discovering synergy between mixtures of existing preservatives and in finding personal care ingredients that may have a coincidental antimicrobial activity (John Woodruff, *Soap Perfumery and Cosmetics*, September, 2006).

Recently, synergistic combinations for enhanced antimicrobial activity of three types of chemical substances, namely, octanoyl component, undecylenoyl component and 'liquid ether alcohol', have been reported (Koshti et al., WO 2013076697). Based on the teachings of this patent application it is apparent that combination of phenoxy ethanol, octanoyl glycine and undecylenoyl glycine would form a potential synergistic preservative system. Individually, all the three components are well-established personal care ingredients. Also, there have been instances where lipidated glycines, N-capryloyl glycine, and N-undecylenoyl glycine have been employed together for their derma-protector/derma-purifier effect. In some cases their usage has been suggested to create seemingly 'preservative-free' formulations.

U.S. Pat. No. 7,214,391 reports use of around 2.5% N-capryloyl glycine or N-undecylenoyl glycine along with glyceryl laurate and glycol to create seemingly 'preservative-free' formulations from botanical extracts such as grape, Irish moss, *yucca* and green tea etc.

Thus, it can be seen that lipidated glycines are being used either alone or together for topical applications. It has also been suggested that these skin actives can perform the function of preservation. N-Undecylenoyl glycine is reported to possess anti-acne activity, when used along with other ingredients like zinc gluconate, capryloyl glycine, plant extracts from rathania, tea, cinnamon, willows or hamemelis (EP0983055).

As mentioned above, recently, synergy between well-known antimicrobials like phenoxy ethanol, N-capryloyl glycine and undecylenoyl monoethanolamide for preservation of personal care products has been reported (WO 2013076697).

However, though expected, the synergy between lipidated glycines and phenoxy ethanol has not been reported so far, particularly, N-undecylenoyl glycine, N-capryloyl glycine and phenoxy ethanol for anti-microbial preservation of personal care ingredients.

Therefore, the present invention aims to provide stable, synergistic, efficacious preservative compositions made up of well accepted personal care ingredients. The proposed compositions are free of controversial parabens, formaldehyde donors, phenolic compounds, halogenated molecules and quaternary ammonium molecules.

OBJECT OF INVENTION i) It is an objective of the present invention to provide a safe, stable, easy-to-use and efficient blend of chemically incompatible personal care ingredients with broad spectrum of antimicrobial activity.
ii) It is another objective of the present invention to develop the formulation of efficient antimicrobials that are safe and not implicated in any controversy over toxicity to humans or the ecosystem.
iii) It is another objective of the present invention to develop energy efficient and eco-friendly technology for preparing a thermodynamically and chemically stable isotropic microemulsion preservative system that would additionally accommodate both water-soluble as well as oil-soluble antimicrobials.

SUMMARY OF INVENTION

In line with the above objectives, the present invention is directed to a chemically and thermodynamically stable, isotropic microemulsion comprising
a) N-acyl glycine (Formula I)

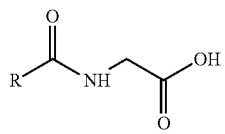

Formula-I wherein R=C7-C10 alkyl or alkenyl group;
b) 2-phenoxy ethanol and
c) water;
wherein, the ratio of lipidated glycine (Formula I) to 2-phenoxy ethanol is 1:3 to 1:5 by weight, water is present from 30 to 60% by weight of the total composition and pH of the composition is at least 6.

All percentages and ratios herein are on weight percent basis unless otherwise stated.

In another aspect, the present invention is directed to a process of producing chemically and thermodynamically stable, isotropic microemulsions. The process in accordance with the invention comprises
a) preparing N-acyl glycine (Formula I) by reacting acyl chloride with glycine in the presence of a base in aqueous medium, acidifying the reaction mass with mineral acid and isolating the N-acyl glycines (Formula I);
b) adding a base to a stirred aqueous suspension of N-acyl glycines of step (a);
c) adding 2-phenoxy ethanol to stirred mass of step (b) to get the optically isotropic, thin microemulsion.

In another aspect, the present invention is directed to personal care compositions containing the preservative microemulsion of the present invention.

The above described features, benefits and advantages of the present disclosures will be appreciated and understood by those skilled in the art from the following detailed description and the claims.

DETAILED DESCRIPTION OF INVENTION

Figure 1:
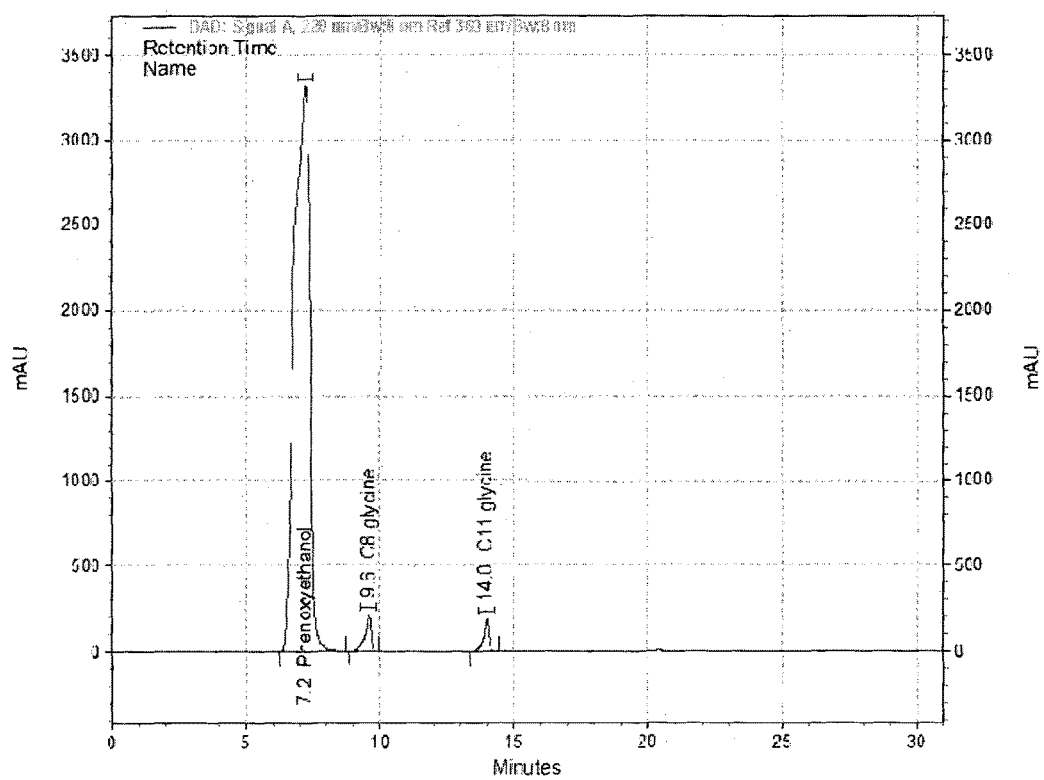
FIG. 1 depicts the Reversed phase chromatography of the ternary microemulsions, wherein there are three distinct peaks corresponding to 2-phenoxy ethanol, N-capryloyl glycine & N-undecylenoyl glycine and confirms that there were no other peak ascertaining no ester impurity formation.

The present invention describes stable microemulsions of N-acyl glycines and 2-phenoxy ethanol for the preservation of personal care products.

In the first aspect, the present invention is directed to a chemically and thermodynamically stable, isotropic microemulsion which comprises:
a) N-acyl glycine (Formula I)

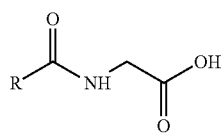

Formula-I wherein R=C7-C10 alkyl or alkenyl group;
b) 2-phenoxy ethanol and
c) water.

In the second aspect, the present invention is directed to a process of producing chemically and thermodynamically stable, isotropic microemulsions. The process in accordance with the invention comprises:
a) preparing N-acyl glycine (Formula I) by reacting acyl chloride with glycine in the presence of a base in aqueous medium, acidifying the reaction mass with mineral acid and isolating N-acyl glycines (Formula I);
b) adding a base to a stirred aqueous suspension of N-acyl glycines of step (a);
c) adding 2-phenoxy ethanol to stirred mass of step (b) to get the optically isotropic, thin microemulsion.

In an embodiment, the ratio of lipidated glycine (Formula I) to 2-phenoxy ethanol is 1:3 to 1:5 by weight.

In another embodiment, water is present from 30 to 60% by weight of total composition.

In yet another embodiment, the pH of the composition is at least 6.

According to yet another embodiment of the present invention, the base used is selected from organic or inorganic base, wherein organic base is selected from fatty tertiary amines such as triethanolamine and inorganic base is selected from potassium hydroxide, ammonium hydroxide or sodium hydroxide, preferably potassium hydroxide or sodium hydroxide is used.

2-Phenoxy Ethanol:

2-phenoxy ethanol or phenoxy ethanol (CAS No. 122-99-6, EC No: 204-589-7), occurs in the nature (green tea) and has been consumed by human race for centuries. It was used as anti-microbial to treat the open wounds of soldiers in the World War II. It is a gentle antimicrobial and is preferred in preserving vaccines that contain very labile proteins. Phenoxy ethanol is more active against Gram negative bacteria (Cosmetic and Drug Preservation, Principles and Practice, Vol I, Ed Jon Kabara, Marcel Dekker). However, in combination with other antimicrobials it shows broad spectrum of activity. Thousands of metric tonnes of phenoxy ethanol is produced all over the world and is considered to be safe with allowed usage level of 1.0% max in personal care products.

Lipidated Glycines:

N-Undecylenoyl Glycine:

Almost four decades ago N-undecylenoyl amino acids were reported for the treatment of skin disorders (JP 49093521, 1974). N-Undecylenoyl glycine (CAS No 54301-26-7) is a well-known derma-purifier with very pronounced anti-acne and anti-dandruff activity.

It is commercially available under the trade name Lipacide UG from Seppic, France. Interestingly, in 2004, use of combination of Wasabi extract along with undecylenoyl glycine as a co-preservative for protection of personal care preparations was reported by D. Misner (US 2004096528). This is an example from the prior art that suggests use of synergistic combination of undecylenoyl derivatives with other ingredients for the purpose of preservation.

N-Capryloyl Glycine:

The other lipidated glycine, N-capryloyl glycine, also known as N-octanoyl glycine (CAS No. 14246-53-8) is also well-known for its action against naturally occurring microflora that is resident of skin. Way back in 1996 it was reported as a non preservative substance that can inhibit microbial growth in cosmetics (Cosmetics & Toiletries, (1996), 17(3), 11-13, 16-19).

It offers derma-protection for the restoration of the skin's acid mantle and purification through dandruff reduction by the inhibition of *Pityrosporum ovale* and sebum reduction through inhibition of 5-alpha reductase. It is commercially available under the trade name of Lipacide C8G from Seppic, France. Its antimicrobial properties, particularly, synergistic action with ethylhexyl glyceryl ether against Gram negative bacteria has been documented in patented literature (EP 0747047).

N-Undecylenoyl Glycine and N-Capryloyl Glycine in Combination:

Cosmetic compositions comprising an N-undecylenoyl glycine and N-capryloyl glycine have been reported in patent application, WO1999027902. A variety of lipidated amino acids (glycine as well as other amino acids) have been formulated for a variety of biological responses. Compositions with N-undecylenoyl glycine and N-capryloyl glycine have been used mainly for their anti-microbial properties against skin's natural flora. Patent application WO2007104879 reports solid powder like mixes made from lipidated amino acids (e.g. N-lauroyl methionine, N-undecylenoyl glycine, N-oleoyl methionine, N-lauroyl proline, N-undecylenoyl phenylalanine and N-octanoyl glycine) for pharmaceutical and dermaceutical applications. Another instance of exploitation of combination of lipidated glycines is a deodorant cream wherein N-undecylenoyl glycine has been used along with aluminium capryloyl glycinate (New Cosmetic Formulations, Mason publications, Hampshire, GB, Vol 443 (43), 2001).

Microemulsions of Phenoxy Ethanol, Water and Lipidated Glycinates as Amphiphiles:

In view of most of the work-horse antimicrobial preservatives being phased out due to either toxicity or environmental concerns, it is imperative that the safer ones be exploited by exploring the synergy amongst them. In this context, it has been invented by the inventors of the present application that the combination of phenoxy ethanol with lipidated glycines, N-capryloyl glycine and N-undecylenoyl glycine, indeed provide a broad antimicrobial activity useful for the purpose of preservation of a variety of personal care products. However, a combinatory mixture (premix) of N-capryloyl glycine, N-undecylenoyl glycine and phenoxy ethanol in the desired ratio is not chemically stable at room temperature due to self-catalyzed esterification of lipidated glycines (carboxyl groups, pKa for capryloyl glycine is 4.05) with phenoxy ethanol, a substance with very reactive primary hydroxyl group. For example, a simple blend of 75% phenoxy ethanol and 25% lipidated glycine is highly unstable at room temperature. The strong acidity of carboxyl group of lipidated glycine catalyzes esterification reaction with the primary hydroxyl group of phenoxy ethanol with the formation of water. The presence of large excess of phenoxy ethanol in such a blend pushes the equilibrium to the right side causing significant generation of corresponding esters, namely, phenoxyethyl N-undecylenoyl glycinate and phenoxyethyl N-capryloyl glycinate at normal temperatures of storage, from 20° C. to 40° C. (Equation 1). This not only results in serious loss of active constituents, the lipidated glycines over the period of short time (six days at ambient temperature results in generation of about 10% undesired esters) but also results in generation of new compounds that could be toxic. The unwanted esterification at ambient temperature could not be arrested or prevented by addition of significant amount of water. Water has limited solubility in phenoxy ethanol (about 9.0% by weight of water is miscible in phenoxy ethanol and 2.3% by weight of phenoxy ethanol is soluble in water). Beyond this limit water is immiscible and saturating phenoxy ethanol with water does not arrest the acid catalyzed esterification between N-acyl glycines and phenoxy ethanol. Thus, adding water to the limit of allowed miscibility (9%) does not stop esterification of lipidated glycines (Formula I) and phenoxy ethanol, particularly when large excess of phenoxy ethanol is still available to push the equilibrium to the ester formation (Equation 1).

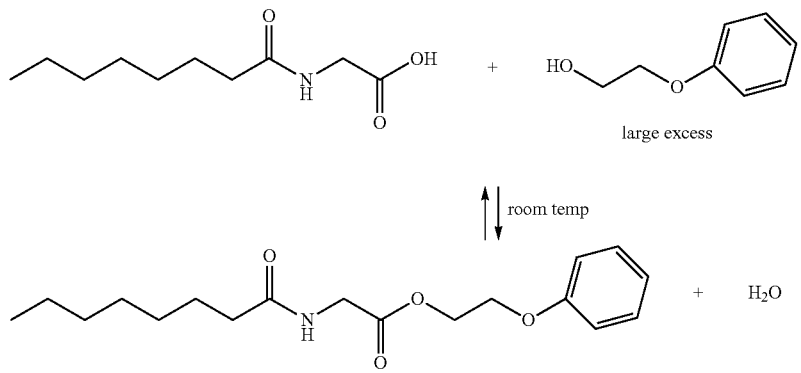

Equation 1

Hence beyond a point, phenoxy ethanol containing lipidated glycines does not solubilize water and the liquids separate into two layers instantaneously. Though only 2.3% phenoxy ethanol gets solubilized in water at room temperature and about 9% water gets solubilized in phenoxy ethanol (Cosmetic and Drug Preservation, Principles and Practice, Vol I, Ed Jon Kabara, Marcel Dekker, page 80-81), the inventors found that it is possible to solubilize higher amounts into each other by creating a microemulsion with the help of other 'desired' antimicrobials. In Example 4 (Table IV of Experimental section), 20 parts of phenoxy ethanol got solubilized through micellar arrangement in 74 parts of water using 5% of lipidated glycinates. The lipidated glycines have been converted into a surface active substance by inorganic bases and five parts of these alkali metal salts of lipidated glycines solubilized 20 parts of phenoxy ethanol in 74 parts of water resulting into a stable isotropic microemulsion. It is possible to have even higher amounts of water solubilized through the intermediacy of lipidated glycinates as exemplified in Example 2 wherein 45 parts of phenoxy ethanol is micellised in about 42 parts of water with about 11 parts of lipidated glycinates to give a stable optically isotropic composition. With higher amount of interfacially active lipidated glycinates (16 parts), it is possible to micellise significantly higher amount of phenoxy ethanol (48 parts) than water (33 parts) to get the isotropic composition as shown in Example 5. Example 3 too, demonstrates a stable micellar arrangement with higher amount of phenoxy ethanol and lesser amount of water. In this example the ratio of lipidated glycines to phenoxy ethanol is 1:4 by weight, whereas in Example 5, the ratio of lipidated glycines to phenoxy ethanol is 1:3 by weight. Example 6 illustrates isotropic microemulsion composition with 1:5: lipidated glycines:phenoxy ethanol by weight whereas, Example 9 of Table V of Experimental section illustrates isotropic composition with the ratio of 1:6. Microemulsion of Example 11 contains an additional water-soluble antimicrobial agent, namely, dehydroacetic acid at 6.5% by weight, thus the total % of antimicrobial agent is about 65%. The microemulsion despite this high loading of antimicrobials is isotropic and thermodynamically stable. On ten times dilution with phenoxy ethanol, the microemulsion of Example 11 still remains transparent and stable. Example 12 illustrates thermodynamically stable microemulsion with inclusion of sorbic acid, another antimicrobial in addition to dehydroacetic acid, lipidated glycines and phenoxy ethanol. The microbes are known to adapt to new environment and become resistant towards the antimicrobials. To prevent microbes from becoming resistant generally they are attacked by more than one substance that inhibit microbial growth by different mechanisms. Hence it is important to be able to create a stable formulation with a variety of non-controversial antimicrobials like benzoic acid, sorbic acid, caprylyl glycol, 2-ethylhexyl glyceryl ether or dehydroacetic acid. Microemulsions of phenoxy ethanol and water can be affected by other surfactants both Non-ionic and Ionic, Ionic, particularly mild surfactants like N-alkanoyl glycinates or sarcosinates or N-alkanoyl,N-methyl taurates. In Example 13 included in the experimental section, sodium lauroyl sarcosinate is employed as the amphiphile to create a thermodynamically stable, isotropic microemulsion containing 40% phenoxy ethanol and 10% lipidated glycines, namely, N-caprylyl glycine and N-undecylenoyl glycine. As mentioned above, the combination attack is always good against microbes so that they do not develop resistance. The microemulsions of the instant invention can include both water-soluble as well as water-insoluble additional antimicrobial ingredients. Example 12 illustrates microemulsion with additional water soluble antimicrobial in the form of dehydroacetic acid whereas Example 14 illustrates incorporation of water-insoluble ethylhexylglycerin (CAS No. 70445-33-9) in the microemulsion (about 2% solubility in water). In Example 15, about 20% water is microemulsified by about 5% of amphiphile and about 75% of 2-ethylhexylglycerin. Microemulsion of Example 15 is completely isotropic and thin liquid and instantaneously formed. In Example 16, about 34% water is microemulsified by about 7% of amphiphile and 45% phenoxy ethanol. The microemulsions of the instant invention prevent the potential acid catalyzed esterification reaction of antimicrobials with a carboxyl group such as N-caprylyl glycine or N-undecylenoyl glycine or sorbic acid with primary hydroxyl groups containing substances that are often used for preservation (phenoxy ethanol or booster of antimicrobials such as ethylhexylglycerin, caprylyl glycol).

It is interesting to note that Example 9 has only one lipidated glycine, namely, N-undecylenoyl glycine and example 10 has only N-caprylyl glycine. All the five examples in Table IV use mixture of lipidated glycines as synthesized by the procedure given in Example 1. The N-acylation of glycine allows flexibility of changing the ratio between two N-alkanoyl glycines, namely, N-capryloyl and N-undecylenoyl glycine. The mixture is produced as sodium salts by reacting corresponding fatty acid chloride with glycine under aqueous conditions in the presence of a base. The aqueous solution of sodium N-Alkanoyl glycinates is then acidified with mineral acid to separate the lipidated glycine as solids. The mixture of lipidated glycines is then filtered and washed with water to remove all water-soluble by-products and the unreacted starting material. It is then used for preparing the microemulsions of Table IV. The microemulsions reported in Table IV and Table V have been made by following the typical procedure given in the experimental section wherein the surface active substance is made in water and to that the oil component (phenoxy ethanol/or other water-insoluble substances like 2-ethylhexylglycerin) is added. Simple agitation results in facile formation of thin isotropic microemulsion within few minutes. This energetically favorable process results in thermodynamically stable microemulsions. The spontaneous formation of thin, low viscous, isotropic thermodynamically stable liquid, that shows Newtonian flow behavior, are all characteristic of a microemulsion. The microemulsions were checked for stability at two temperatures of 20° C. and 40° C. for three months and chromatographed (Reversed phase chromatography, C18 bonded column, mobile phase-acetonitrile-water, UV detection at 220 nm) periodically to ascertain the chemical stability. Three distinct peaks corresponding to phenoxy ethanol, N-capryloyl glycine & N-undecylenoyl glycine were observed (FIG. 1) and there were no other peak ascertaining no ester impurity formation. The solidification points of microemulsion are 0° C. or below. The frozen microemulsions when thawed to ambient temperature return to original isotropic and thermodynamically stable nature.

Figure 2:
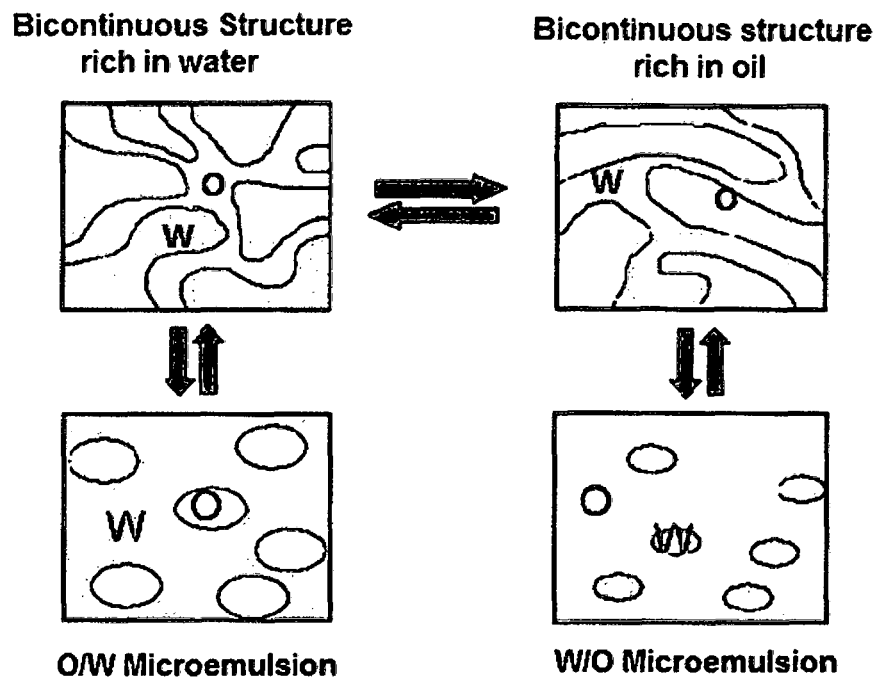
FIG. 2 shows systems with ordered 'bicontinuous' microemulsions that can be in equilibrium with O/W and W/O microemulsions.
Figure 3:
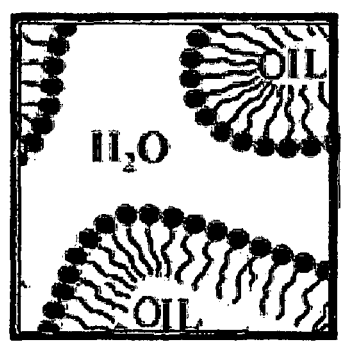
FIG. 3 shows the structural arrangement of a bicontinuous microemulsion with ternary system of oil, water and amphiphile.

In this ternary microemulsion (oil (phenoxy ethanol in this case), water and amphiphile (lipidated glycinates)), the amphiphiles can be created with a variety of bases such as potassium hydroxide or ammonium hydroxide or the organic amines. Based on the solubility of surface active agents, the microemulsions of present invention can be O/W type. Microemulsion of Example 4 can be diluted with water and after 10 times dilution it remains isotropic. Similarly, microemulsions of Examples 2, 3, 5, and 6 of Table IV remained isotropic after 10 times dilution with phenoxy ethanol. These compositions could be the cases of 'swollen micelles' or W/O type of microemulsions. However, considering the facile nature of formation of microemulsions (Table IV and Table V) and their dilution behavior it is very likely that the systems are more like ordered 'bicontinuous' microemulsions that can be in equilibrium with O/W and W/O microemulsions (FIG. 2). The structural arrangement of a bicontinuous microemulsion with ternary system of oil, water and amphiphile is shown in FIG. 3 (M. R. Porter, Chapter 3, Handbook of Surfactants, Blackie Academic & professional (1994), pg 57-61) Microemulsions of Examples 2, 3, 5 & 6 have about 55 to 65% of antimicrobials, the lipidated glycines and phenoxy ethanol. Microemulsion of Example 3 with 13% lipidated glycines and 52 phenoxy ethanol is taken for further study for the antimicrobial activity against a variety of organisms. MIC numbers (minimum inhibitory concentration) of Example 3 against Gram positive (*Staphylococcus aureus*), Gram negative (*Pseudomonas aeruginosa*) bacteria and against yeast (*Candida albicans*) and mold (*Aspergillus niger*) are tabulated in Table I. The microemulsion shows reasonable activity against acne causing *Propiniobacterium acnes* and dandruff causing *Malassezia furfur*.

TABLE I

| Microorganism | MIC of Example 3 (% active) |
|---|---|
| *Staphylococcus aureus* ATCC 6538 | 0.6 |
| *Pseudomonas aeruginosa* ATCC 15442 | 0.4 |
| *Escherichia coli* ATCC 8739 | 0.5 |
| *Candida albicans* ATCC 10231 | 0.6 |
| *Aspergillus niger* ATCC 16404 | 0.5 |
| *Propiniobacterium acnes* MTCC 1951 | 0.8 |
| *Malassezia furfur* MTCC 1374 | 0.7 |
| *Salmonella choleraesuis* ATCC 10708 | 0.4 |
| *Enterococcus hirae* ATCC 10541 | 0.7 |

The preservation efficacy of microemulsion of Example 3 was tested by incorporating it in two types of personal care formulations that have significant quantity of water, namely, a shampoo (rinse-off application, Example 17) and an oil-in-water cream formulation (leave-on application, Example 18) at about 1.2% active level. Both formulations were then challenged by inoculating with various microbes as per the standard protocol of CTFA ('Evaluation of preservatives to protect cosmetics' by D. Orth in *Cosmetics and Toiletries*, March 91). The initial inoculation level of microbes for this study was $10^8$ to $10^{10}$ cfu/ml. Both samples survived the challenge tests and the results are tabulated in Tables II and III.

TABLE II

Challenge test in shampoo formulation

| TVC in Cfu/gm | 1 hrs | 24 hrs | 48 hrs | 7 day | 14 day | 21 day | 28 day |
|---|---|---|---|---|---|---|---|
| *Escherichia coli* ATCC 8739 | $1 \times 10^5$ | $6 \times 10^2$ | <10 | <10 | <10 | <10 | <10 |
| *Staphylococcus aureus* ATCC 6538 | $38 \times 10^3$ | $9.6 \times 10^3$ | $4.9 \times 10^3$ | <10 | <10 | <10 | <10 |
| *Pseudomonas aeruginosa* ATCC 15442 | $9 \times 10^2$ | <10 | <10 | <10 | <10 | <10 | <10 |
| *Candida albicans* ATCC 10231 | $62.13 \times 10^4$ | $1 \times 10^2$ | <10 | <10 | <10 | <10 | <10 |
| *Aspergillus niger* ATCC 16404 | $9.5 \times 10^4$ | $8 \times 10^3$ | $4.13 \times 10^2$ | $4.33 \times 10$ | <10 | <10 | <10 |
| *Malassezia furfur* MTCC 1374 | $3.65 \times 10^5$ | $11.89 \times 10^5$ | $6.94 \times 10^5$ | <10 | <10 | <10 | <10 |
| *Propiniobacterium acnes* MTCC 1951 | $15.55 \times 10^5$ | $55.75 \times 10^5$ | $1.18 \times 10^8$ | <10 | <10 | <10 | <10 |

TABLE III

Challenge test in cream formulation

| TVC in Cfu/gm | 1 hrs | 24 hrs | 48 hrs | 7 day | 14 day | 21 day | 28 day |
|---|---|---|---|---|---|---|---|
| *Escherichia coli* ATCC 8739 | $3 \times 10^3$ | <10 | <10 | <10 | <10 | <10 | <10 |
| *Staphylococcus aureus* ATCC 6538 | $4 \times 10^4$ | <10 | <10 | <10 | <10 | <10 | <10 |
| *Pseudomonas aeruginosa* ATCC 15442 | $2 \times 10^2$ | <10 | <10 | <10 | <10 | <10 | <10 |
| *Candida albicans* ATCC 10231 | $3.9 \times 10^5$ | $5.1 \times 10^4$ | <10 | <10 | <10 | <10 | <10 |
| *Aspergillus niger* ATCC 16404 | $6 \times 10^6$ | <10 | <10 | <10 | <10 | <10 | <10 |
| *Malassezia furfur* MTCC 1374 | $5.66 \times 10^5$ | $0.85 \times 10^4$ | <10 | <10 | <10 | <10 | <10 |
| *Propiniobacterium acnes* MTCC 1951 | $21.2 \times 10^6$ | $4.65 \times 10^3$ | <10 | <10 | <10 | <10 | <10 |

EXAMPLES

The present invention is now described by way of working on limiting illustrative examples. The detail of the invention provided in the following examples is given by the way of illustration only and should not be construed to limit the scope of the present invention.

Galaxy LES 70, Galaxy 100 and Galaxy 610 were procured from Galaxy Surfactants Ltd. Mineral oil and glyceryl monostearate were purchased from Apar Industries and Fine organics Pvt Ltd. Stearic acid, cetostearyl alcohol, octanoic acid and undecylenic acids have been procured from VVF Ltd.

Example 1: Synthesis of Blend of N-Undecylenoyl Glycine and N-Capryloyl Glycine To a stirred mixture of glycine (225 g, 3.0 gmol) in water (1700 g) at 25° C. under nitrogen, is added mixture of capryloyl chloride (255 g, 1.54 gmol) and undecylenoyl chloride (255 g, 1.24 gmol) and sodium hydroxide solution (478 g of 48.5% aqueous solution, 5.8 mmol) simultaneously while maintaining temperature between 20 to 25° C. and pH between 9.5 to 10.5. The addition takes 4 to 5 hours depending on the efficiency of temperature control. The reaction mass is stirred for additional two hours. It is further acidified by addition of concentrated hydrochloric acid. The precipitated solid is filtered and washed with plenty of water to remove the mineral acidity. The mixture of lipidated glycines is obtained as solid powder (595 g, 95%) after vacuum drying at 65° C. The dried powder had moisture content less than 1% and acid value of 258. The HPLC analysis of the powder indicated it to nearly 50:50 ratio of N-undecylenoyl glycine and N-capryloyl glycine. The mixture melts at 90 to 95° C.

Examples 2 to 10: The Isotropic Microemulsions are Prepared Following a Typical Procedure Given Below To a stirred suspension of N-undecylenoyl glycine and N-capryloyl glycine from Example 1 in water at room temperature, sodium hydroxide flakes are added gradually ensuring no increase of the temperature of the reaction mass. To this stirred mass, phenoxy ethanol is added and the reaction mass is stirred at room temperature till it becomes homogeneous and transparent. The results are tabulated below in tables IV and V.

TABLE IV

| Blend No. | Lipidated glycines of Example 1 % w/w | Phenoxy ethanol (PE) % w/w | Water % w/w | NaOH flakes % w/w | pH |
|---|---|---|---|---|---|
| Example 2 | 11.2 | 45 | 41.8 | 2. | 7.50 |
| Example 3 | 13 | 52 | 32.5 | 2.5 | 6.5 |
| Example 4 | 5 | 20 | 74 | 1.0 | 7.0 |
| Example 5 | 16 | 47.5 | 33 | 3.5 | 6.5 |
| Example 6 | 11 | 55 | 31.5 | 2.5 | 7.00 |

TABLE V

| Blend No. | N-capryloyl Glycine % w/w | N-undecylenoyl Glycine % w/w | Undecylenoyl MEA amide % w/w | PE % w/w | Water % w/w | NaOH % w/w | pH % |
|---|---|---|---|---|---|---|---|
| Ex 7 | 8 | | 8 | 48 | 34.4 | 1.6 | 6.5 |
| Ex 8 | | 8 | 8 | 48 | 34.6 | 1.4 | 6.5 |
| Ex 9 | | 8 | | 48 | 42.6 | 1.4 | 6.5 |
| Ex 10 | 15 | | | 45 | 37.1 | 2.9 | 6.4 |

Example 11: Microemulsion with Phenoxy Ethanol, Lipidated Glycines, Water and Dehydroacetic Acid To a stirred suspension of N-undecylenoyl glycine and N-capryloyl glycine (13 g) from Example 1 in water (33.5 g) at room temperature, sodium hydroxide flakes (2.45 g) are added gradually ensuring no increase of the temperature of the reaction mass. To this stirred mass, dehydroacetic acid (6.5 g), followed by phenoxy ethanol (45.0 g) is added and the reaction mass is stirred at room temperature till it becomes homogeneous and transparent instantaneously. The pH is adjusted to 6.5 with caustic lye to afford the pale yellow thin isotropic microemulsion.

Example 12: Microemulsion with Phenoxy Ethanol, Lipidated Glycines, Water, Dehydroacetic Acid and Sorbic Acid To a stirred suspension of N-undecylenoyl glycine and N-capryloyl glycine (13 g) from Example 1 in water (33.5 g) at room temperature, sodium hydroxide flakes (2.45 g) are added gradually ensuring no increase of the temperature of the reaction mass. To this stirred mass, dehydroacetic acid (3.5 g) and sorbic acid (3.0 g) followed by phenoxy ethanol (45.0 g) is added and the reaction mass is stirred at room temperature till it becomes homogeneous and transparent instantaneously. The pH is adjusted to 6.5 with caustic lye to afford the pale yellow thin isotropic microemulsion.

Example 13: Microemulsion with Phenoxy Ethanol, N-Capryloyl Glycine, N-Undecylenoyl Glycine, Water and Another Anionic Surfactant, Sodium Lauroyl Sarcosinate To a stirred solution of sodium lauroyl sarcosinate (30 g in 70 ml water), phenoxy ethanol (80 g) is added. A few minutes of stirring resulted in a clear thin solution. To this thermodynamically stable isotropic ternary microemulsion, N-undecylenoyl glycine (10 g) and N-capryloyl glycine (10 g) are added and stirring continued for a few minutes till a transparent solution is obtained. The pH of this solution is around 5.0.

Example 14: Microemulsion with Phenoxy Ethanol, Ethylhexylglycerin, N-Capryloyl Glycine, N-Undecylenoyl Glycine and Water To a stirred suspension of N-undecylenoyl glycine and N-capryloyl glycine (13 g) from Example 1 in water (33.5 g) at room temperature, sodium hydroxide flakes (2.45 g) are added gradually ensuring no increase of the temperature of the reaction mass. To this stirred mass, 2-ethylhexylglycerin (10 g) followed by phenoxy ethanol (35.0 g) is added and the reaction mass is stirred at room temperature till it becomes homogeneous and transparent instantaneously. The pH is then adjusted to 6.5 with caustic lye to afford colorless thin isotropic microemulsion.

Example 15: Microemulsion with Ethylhexylglycerin, N-Capryloyl Glycine, N-Undecylenoyl Glycine and Water To a stirred suspension of N-undecylenoyl glycine and N-capryloyl glycine (5 g) from Example 1 in water (20 g) at room temperature, sodium hydroxide flakes (1.0 g) are added gradually ensuring no increase of the temperature of the reaction mass. To this stirred mass, 2-ethylhexylglycerin (74 g) is added and the reaction mass is stirred at room temperature till it becomes homogeneous and transparent instantaneously. The pH is then adjusted to 6.5 with caustic lye to afford colorless thin isotropic microemulsion.

Example 16: Microemulsion with Dehydroacetic Acid, Benzoic Acid, Phenoxy Ethanol, N-Capryloyl Glycine, N-Undecylenoyl Glycine and Water To a stirred suspension of N-undecylenoyl glycine (6.0 g) and N-capryloyl glycine (6.0 g) in water (60 g) at room temperature, sodium hydroxide (6.5 g) flakes are added gradually ensuring no increase of the temperature of the reaction mass. To it is added dehydroacetic acid (8 g) and benzoic acid (12 g). To this stirred mass, phenoxy ethanol (80 g) is added and the reaction mass is stirred at room temperature till it becomes homogeneous and transparent. The pH is then adjusted to 6.5 with caustic lye to afford colorless thin isotropic microemulsion.

Example 17: Preparation of Shampoo: Preservation with Microemulsion of Example 3

| Components | Trade Name | (% W/W) |
|---|---|---|
| Phase A | | |
| Water (Aqua) | D.M. Water | 70.00 |
| Sodium laureth sulphate (70%, 2 EO) | Galaxy LES 70 | 20.00 |
| Phase B | | |
| Cocomonoethanol amide | Galaxy 100 | 3.00 |
| Ethylene glycol distearate | Galaxy 610 | 2.00 |
| Phase C | | |
| Preservative | Microemulsion of Example 3 | 2.00 |
| Citric acid 50% | | q.s. to pH 6 to 6.5 |
| Fragrance, Color | | q.s |

Procedure:

All the ingredients of phase A were heated to 75° C. under slow stirring. Added phase B and mixed until homogeneous. The reaction mass was cooled to room temperature and added phase C, stirred until uniform. The pH of the final formulation was adjusted with 50% citric acid and blended with fragrance and color.

Example 18: Preparation O/W Cream: Preservation with Microemulsion of Example 3

| Components | Trade Name | (% W/W) |
|---|---|---|
| Phase A | | |
| Water (Aqua) | D.M. Water | 70.00 |
| Glycerin | Glycerin | 2.00 |
| Paraffinum Liquidum | Mineral oil | 15.00 |
| Stearic Acid | Stearic Acid | 2.00 |
| Glyceryl Stearate | Glyceryl Stearate | 5.00 |
| Cetearyl Alcohol | Cetearyl Alcohol | 3.50 |
| Phase C | | |
| Preservative | Microemulsion of Example 3 | 2.00 |
| Fragrance, Color | | q.s |

Procedure:

Heated Phase A, and Phase B separately to 75° C. with stirring. Added phase B to phase A with constant stirring and homogenise the mixture for 2 minutes and continued stirring for 15 minutes. The reaction mass was cooled to 40° C. and added phase C, mixed well and blended with fragrance and color.

ADVANTAGES OF THE INVENTION

1) The microemulsions (micellar solutions) of the present invention are based on the personal care ingredients that are cosmetically well accepted, with proven benefits (derma-purifier effect, anti-acne and anti-dandruff) and are completely biodegradable.

2) The microemulsions of this patent application are made from personal care ingredients. 2-Phenoxy ethanol, an established, non-controversial preservative, is produced worldwide by several manufacturers on the scale of thousands of metric tonnes and is one of the cheapest ingredients due economy of large scale manufacture. The other two, lipidated glycines are based on octanoic acid and undecylenic acids and are manufactured by a facile one-pot synthesis of this patent application that allows any ratio of N-undecylenoyl glycine to N-capryloyl glycine. This makes these 'three component' microemulsion (oil (phenoxy ethanol in this case), water and surfactant (lipidated glycines)) very cost-effective. The compositions are also designed to give the best broad spectrum performance at the least of the cost.

3) The isotropic thin microemulsions of the present invention are chemically and thermodynamically stable between temperatures of 20° C. to 40° C. These allow blending of two types of inherently incompatible antimicrobials in a chemically and thermodynamically stable system which is very useful to create several synergistic combinations of antimicrobials. The inherently incompatible and reactive substances are the ones with carboxyl group and primary hydroxyl group. Examples are N-capryloyl glycine or N-undecylenoyl glycine and phenoxy ethanol. Though phenoxy ethanol and lipidated glycines in personal care formulations address the global issue of preservation, they are not stable together. This problem of unwanted reactivity has been resolved by the microemulsions of the present invention.

The microemulsions of the present invention allow combinations of several antimicrobials in chemically and thermodynamically stable compositions that are 'easy-to-incorporate'. Antimicrobials or antimicrobial activity boosters can be either oil-soluble or water-soluble. Use of multi-antimicrobial always has its advantage of lowering dosage of individual substance and microbes are inhibited from being resistant over a long period of time.

4) The microemulsions for the protection of topical products described in this patent application are free of controversial a) parabens b) 'formaldehyde releasing' substances (urea derivatives, Quaternium 15) c) isothiazolinones (methyl and chloromethyl) and halogenated molecules (chloro/bromo/iodo derivatives).

5) The preservative microemulsions of the instant invention are designed to obtain the wide range of antimicrobial activity and are active against Gram positive, Gram negative bacteria, yeast and mould.

6) Additional benefit of derma-purification and derma-protection in case of 'leave-on' products is expected at the levels at which these microemulsions are used as preservatives. The lipidated glycines are active against normal skin flora and reported to provide the protective 'acid-mantle' to skin.

7) The microemulsions (micellar compositions) of the present patent application are compatible with all cosmetic ingredients, stable towards any oxidizing or reducing agents and within the normal range of pH (4.0 to 7.0) of personal care formulations.

8) The microemulsions of the present invention have lower freezing point (0° C.) than phenoxy ethanol (15° C.) which helps in transportation and storage during winter. The microemulsions if frozen below zero degree Celsius can be thawed to their normal homogeneous isotropic nature.

Anyone with the reasonable level of knowledge of the art would understand that these stable aqueous micellar preservative systems can be used with additional anti-microbial compounds or adjuvants that can enhance or boost antimicrobial activity synergistically. The examples of such adjuvants are ethylhexyl glyceryl ether, caprylyl glycol, 1,3-propane diol or EDTA etc.

We claim:

1. A chemically and thermodynamically stable, isotropic microemulsion, comprising
   a) N-acyl glycine (Formula I)

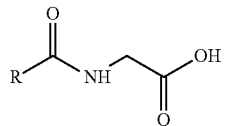

Formula-I wherein R=C7-C10 alkyl or alkenyl group;
   b) 2-phenoxy ethanol and
   c) water,
   wherein the pH of the microemulsion is at least 6.

2. The microemulsion according to claim 1, wherein N-acyl glycine (Formula I) is N undecylenoyl glycine, N capryloyl glycine, or a mixture thereof.

3. The microemulsion according to claim 1, wherein the ratio of N-acyl glycine (Formula I) to 2-phenoxy ethanol is 1:3 to 1:5 by weight.

4. The microemulsion according to claim 1, wherein the amount of water is from 30 to 60% by weight of the microemulsion.

5. The microemulsion according to claim 1, which is freeze-thaw stable.

6. A process of producing a chemically and thermodynamically stable, isotropic microemulsion according to claim 1, comprising steps of
   a) preparing an N-acyl glycine (Formula I) by reacting an acyl chloride with glycine in the presence of a base in aqueous medium, acidifying the reaction mass with mineral acid and isolating the N-acyl glycine (Formula I);
   b) adding a base to a stirred aqueous suspension of the N-acyl glycine of step (a) and
   c) adding phenoxy ethanol to stirred mass of step (b) to get the optically isotropic, thin microemulsion.

7. The process according to claim 6, wherein the base used in step (a) and (b) is potassium hydroxide, sodium hydroxide, or a mixture thereof.

8. The process according to claim 6, wherein the pH of the microemulsion is at least 6.

* * * * *